(12) United States Patent
Faber et al.

(10) Patent No.: US 7,072,497 B2
(45) Date of Patent: Jul. 4, 2006

(54) METHOD FOR OPERATING A MEDICAL IMAGING EXAMINATION APPARATUS

(75) Inventors: Roland Faber, Uttenreuth (DE); Rainer Kuth, Herzogenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 922 days.

(21) Appl. No.: 10/071,491

(22) Filed: Feb. 7, 2002

(65) Prior Publication Data

US 2002/0114500 A1   Aug. 22, 2002

(30) Foreign Application Priority Data

Feb. 7, 2001   (DE) .................. 101 05 585

(51) Int. Cl.
*G06K 9/00* (2006.01)

(52) U.S. Cl. ..................................... 382/128

(58) Field of Classification Search ........ 382/128–134, 382/254, 274; 324/309, 312; 378/206
See application file for complete search history.

(56) References Cited

U.S. PATENT DOCUMENTS

| 5,239,266 A | 8/1993 | Kaufman et al. | |
| 5,436,563 A * | 7/1995 | Kuth et al. | 324/312 |
| 5,577,095 A * | 11/1996 | Kobayashi | 378/206 |
| 6,121,775 A * | 9/2000 | Pearlman | 324/309 |
| 6,700,374 B1 * | 3/2004 | Wu et al. | 324/312 |

FOREIGN PATENT DOCUMENTS

DE   197 20 438   11/1998

* cited by examiner

*Primary Examiner*—Kanjibhai Patel
(74) *Attorney, Agent, or Firm*—Schiff Hardin LLP

(57) ABSTRACT

In a method for operating an imaging medical examination apparatus and an apparatus operating according to the method, particularly a magnetic resonance apparatus, measured signals of an examination subject are sequentially registered and processed by an image computer into outputtable image data signals of an individual image or a series of images, and the image data of an individual image or a series of images are interpreted with reference to at least one diagnosis-specific parameter that represents a criterion for the image quality to be achieved and that is predetermined, for the individual image or image series. Dependent on the evaluation result, the measured signal acquisition is ended when the prescribed parameter is satisfied or is continued until a renewed interpretation shows that the prescribed parameter has been met.

20 Claims, 2 Drawing Sheets

METHOD FOR OPERATING A MEDICAL IMAGING EXAMINATION APPARATUS

BACKGROUND OF THE INVENTION

1. Field of the Invention

The present invention is directed to a method for operating a medical imaging examination apparatus, particularly a magnetic resonance apparatus, wherein measured signals of an examination subject are sequentially registered and are processed by an image computer into image data signals for an individual image and a series of images.

2. Description of the Prior Art

Magnetic resonance apparatuses are being increasingly utilized for obtaining images in the examination of patients, since they enable a relatively stress-free examination of the patient as well as the assessment of a large variety of body areas. The basic functioning of magnetic resonance apparatus is well-known. To an increasing degree, however, there is a demand for reproducibility of the registered examination results or of the registered images. This is required in order, for example, to be able to compare images respectively registered with a time offset therebetween or images registered with different magnetic resonance apparatuses. Independently of location and time of examination, the result should always be essentially the same or at least comparable.

This, however, is not possible due to the standard operating method of known magnetic resonance apparatus. The quality of the registered images is highly dependent on the ability, the motivation and the experience of the operator, as well as on the quality of the magnetic resonance apparatus, the preceding anamnesis, the perception of the patient and other factors. Reproducibility is usually hardly possible due to these many factors affecting the image quality, which are mostly of a subjective nature and dependent on the participating persons. Added thereto as a complicating factor is that an attempt is always made to keep the examination duration optimally short in order to keep the operating time of the device per examination patient as short as possible and, thus, to obtain a system work throughput that is as high as possible. Ultimately, this operating mode leads to highly fluctuating quality standards and to a frequent change in physicians, since patients are re-examined by a different physician after an examination that seems unsatisfactory.

SUMMARY OF THE INVENTION

An object of the present invention is to provide an operating method for a medical imaging examination apparatus, particularly for a magnetic resonance apparatus, as well as a corresponding, imaging medical examination apparatus, particularly a magnetic resonance apparatus, wherein a reproducible image exposure is possible.

This object is inventively achieved in a method and apparatus of the type initially described wherein the image data of an individual image, or a series of images, are interpreted with reference to at least one diagnosis-specific parameter that represents a criterion for the image quality to be achieved and that is predetermined, related to the individual image or related to the image series, and wherein the measured signal acquisition is ended dependent on the evaluation result when the prescribed parameter is satisfied, or is continued until a renewed interpretation shows that the prescribed parameter has been met.

In the inventive method and apparatus a prescription related to image quality in the form of the individual image-related or image series-related parameter is specified for each examination, which represents a quality criterion for the individual image or the image series that is to be met by the individual image or by the image series. The parameter is diagnosis-specific, i.e. it is specifically adapted to the diagnostic question underlying the examination. Dependent on the purpose of the examination, this makes it possible to make a corresponding quality prescription of the image or image series, since different patient areas are to be examined dependent on the diagnostic question, or the image presentation must contain different, diagnostic-specific image information dependent on the diagnostic question. The parameter that is to form the basis for the prescription is selected by the examination apparatus or magnetic resonance apparatus by an input of the corresponding patient and examination information (for example, information about the person of the patient such as age, weight, etc., as well as information about the examination region, the diagnostic question, etc.). The parameter is selected from a stored family of parameters. Alternatively, of course, there is also the possibility for the operator to personally select the quality-defining parameter or parameters, or to add this to the parameters selected on the part of the apparatus.

In operation of the apparatus, i.e. during the acquisition of the measured signal, a slice of the patient is initially measured in the case of a magnetic resonance examination and the image data signals are subsequently reconstructed by a Fourier transformation. Subsequently, the image data signals obtained as a result are evaluated with reference to the prescribed parameter or parameters, i.e. a check is made to determine whether the image data signals that have already been registered are adequate and whether the parameter prescription has been met. If the parameter prescription has been met, this means that the quality prescriptions made for the individual image or the image series by the predetermined parameter have been met, i.e. the image or the image series meets a minimum quality. The exposure can then be ended. If the evaluation shows that the prescribed parameter or parameters has/have not yet been met, then the measured signal registration is continued, i.e. the measured slice is investigated further, with a renewed evaluation being undertaken after another measurement of the slice. This may show that the quality demands now have been met, whereupon the signal registration, and thus the image registration, is ended. If the re-evaluation still shows that the quality prescriptions have not yet been met, then the examination is continued. Preferably, the examination is aborted after a prescribable number of unsuccessful evaluations and/or after a prescribable time span with a negative message if the prescribed parameters have not been met The negative message is emitted as an output, for example, acoustically, optically and/or in writing in the documentation papers.

Since the parameters are predetermined minimum quality criteria that an image or an image series must at least exhibit, the inventive method and apparatus allow adequate reproducible image acquisition. Images registered at different points in time or with different examination apparatus or different magnetic resonance apparatuses are always based on the same quality-defining parameter or parameters, so that the images ultimately exhibit the same or a very similar minimum quality. Time-offset diagnoses on the basis of different images are thus unproblematically possible for the attending physician. The inventive method and apparatus thus offer the possibility of making a target designation of the image quality, the attainment thereof being monitored by the system itself during the examination and only leading to a positive termination of the examination when the goal has been reached. Thus, the examination duration is no longer defined by the purely subjective ability of the operator but instead by the examination apparatus or magnetic resonance apparatus itself, and controls the operation until an optimum image is present with reference to the diagnostic question, and thus with reference to the diagnostic-specific parameter. The inventive imaging medical examination apparatus, particularly a magnetic resonance apparatus, that is suitable for the implementation of this method consequently can be operated by persons having little experience.

The predetermined parameters can be of an arbitrary type as long as they characterize a qualitative image feature. For example, an image contrast-related parameter can be employed as the parameter, with the individual image or the image series being evaluated with respect to the contrast of one or more image regions. When, for example, the brain of a patient is to be examined, then the image-related parameter can define the contrast between white brain matter and grey brain matter that the image or the image series must exhibit at a minimum. The parameter can define the relationship of the grey scale values of two image regions.

As a possible further parameter, a parameter that is related to the image data signal can be employed, this being a criterion for the signal curve of the image signal. This parameter that, for example, can define the signal amplitude and/or the slope of the signal edge (or edges) and/or the ratio of amplitude to waveform width (i.e., the distance between two points of equal magnitude in a waveform), thus defines the quality on the basis of the curve of the registered image signal. For example, this is expedient in the framework of vessel examinations wherein the vessel structure leads to signal curves that can be easily interpreted.

Additionally, for checking the stability of the image exposure, at least two, preferably more than two of successively registered images are interpreted to determine whether an image parameter, for example the contrast or the brightness of an image region changes within a limit defined with the parameter, with further measured signals, and thus images, being registered given too great a change. This stability check is expedient, for example, in functional examinations such as, for example, those for defining the BOLD effect (BOLD=blood oxygen level detection), where areas with an increased oxygen region indicating that defined stimuli are being processed therein, are rendered visible with magnetic resonance examination. It can be determined whether an adequate number of images have already been registered and the image registration is stable, when as nothing or hardly anything changes in the most recently registered images or whether sufficient images have not yet been registered and changes still occur. A check can also be made to determine whether an improvement can be obtained at all as a result of the image exposure. When, for example, a first parameter is prescribed with respect to the contrast of two image regions and a defined limit is indicated as a second parameter, then an examination can be terminated which, due to a faulty slice position or the like, necessarily leads to images that do not meet the first, contrast-related parameter. When, the measured slice has been placed incorrectly, then the prescribed contrast can never be achieved and this would lead to an unending continuation of the image registrations since the interpretation always shows that the parameter has not yet been met. A determination can be made via the second parameter defining the change limit that no changes, and thus no image improvements, are occurring despite repeated image registration, so that the measurement can be aborted and the de facto unsatisfactory result can be recognized.

DESCRIPTION OF THE PREFERRED EMBODIMENTS

Figure 1:
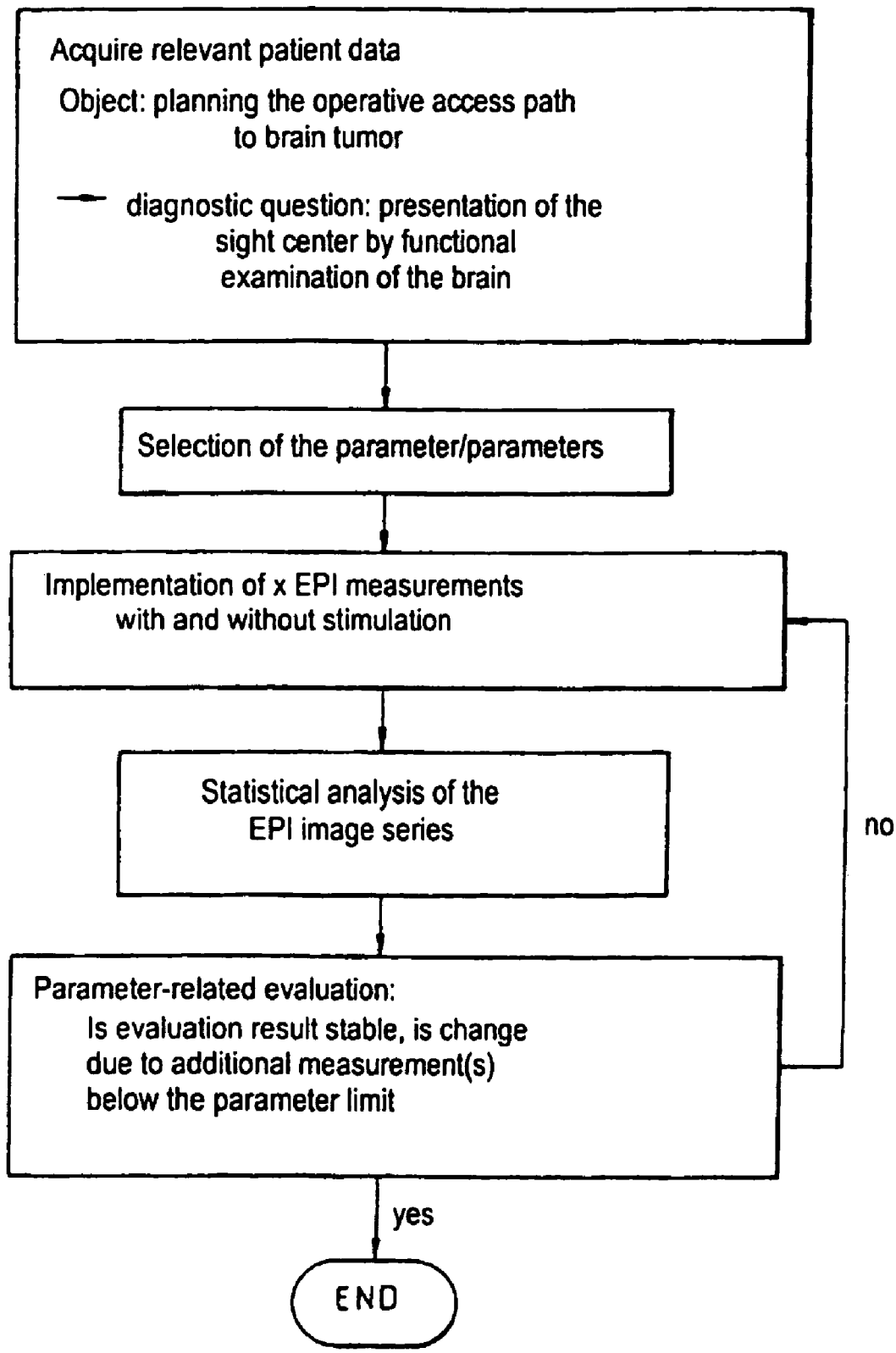
FIG. 1 is a flow chart of a first exemplary examination conducted in accordance with the inventive method using an inventive apparatus.

In the form of a flow chart, FIG. 1 shows the executive sequence of a first exemplary examination that can be implemented with the inventive magnetic resonance apparatus. The examination is based on the problem or object of planning the operative access route to a tumor region for a brain operation. The presentation of the sight center forms the basis for the examination as the diagnostic question. To this end, a functional examination of the brain is undertaken with the magnetic resonance apparatus. In the framework of this examination for presenting the sight center, the BOLD effect (BOLD=blood oxygen level detection) is examined. Areas having increased oxygen consumption are thereby rendered visible with the magnetic resonance. This increased oxygen consumption occurs as a consequence of processing stimuli. Within the framework of the functional examination, measurements with and without defined stimulation of the sight center are successively implemented. The stimulation ensues, for example, with simple illumination into the eyes of the patient. On the basis of the registered measurements with and without stimulation, the sight center can then be rendered visible on the basis of brighter image regions that represent regions of increased oxygen consumption.

Proceeding on the basis of the object underlying the examination and on the basis of the diagnostic question, the relevant patient data are initially acquired. The patent data are characteristic of the patient, for example the body mask, the age, potential sicknesses and the like. Such data also are relevant for the measurement to be implemented since specific operating parameters are set dependent thereon.

The relevant parameter or parameters defining the required minimum image quality is/are subsequently automatically selected, for example at the apparatus. In the illustrated exemplary embodiment, only one parameter is selected as an example, this setting a limit with respect to possible changes in successively registered images in order to be able to make a conclusion about the stability of the image registration on the basis of these changes. The recognizability of the sight center improves in the framework of the functional examination with increasing number of measurements, until reaching a point where the recognizability of the sight center hardly changes or does not change at all with a further of measurement. The selected parameter then defines a change limit that defines a degree of change of a threshold below which the change within two images must lie in order to be able to assume an adequate image stability.

After selection of the parameter, an arbitrary number x of EPI measurements (EPI=echoplanar imaging) are implemented. Echoplanar imaging is an ultra-fast imaging method with measuring times that are typically below one second. The measurements are implemented in alternation with and without stimulation. A statistical analysis of the registered EPI image series subsequently ensues. This is followed by the parameter-related evaluation. A check is made to determine whether the statistical analysis result is stable, i.e.

within a change as a result of an additional measurement or additional measurements lies below the defined parameter limit. When this is the case, then the image registration is adequately stable, a further improvement of the presentation of the sight center, if possible at all, is only possible to an insignificant degree. When the parameter-related evaluation yields that the image registration is not yet stable, then further EPI measurements are implemented.

Figure 2:
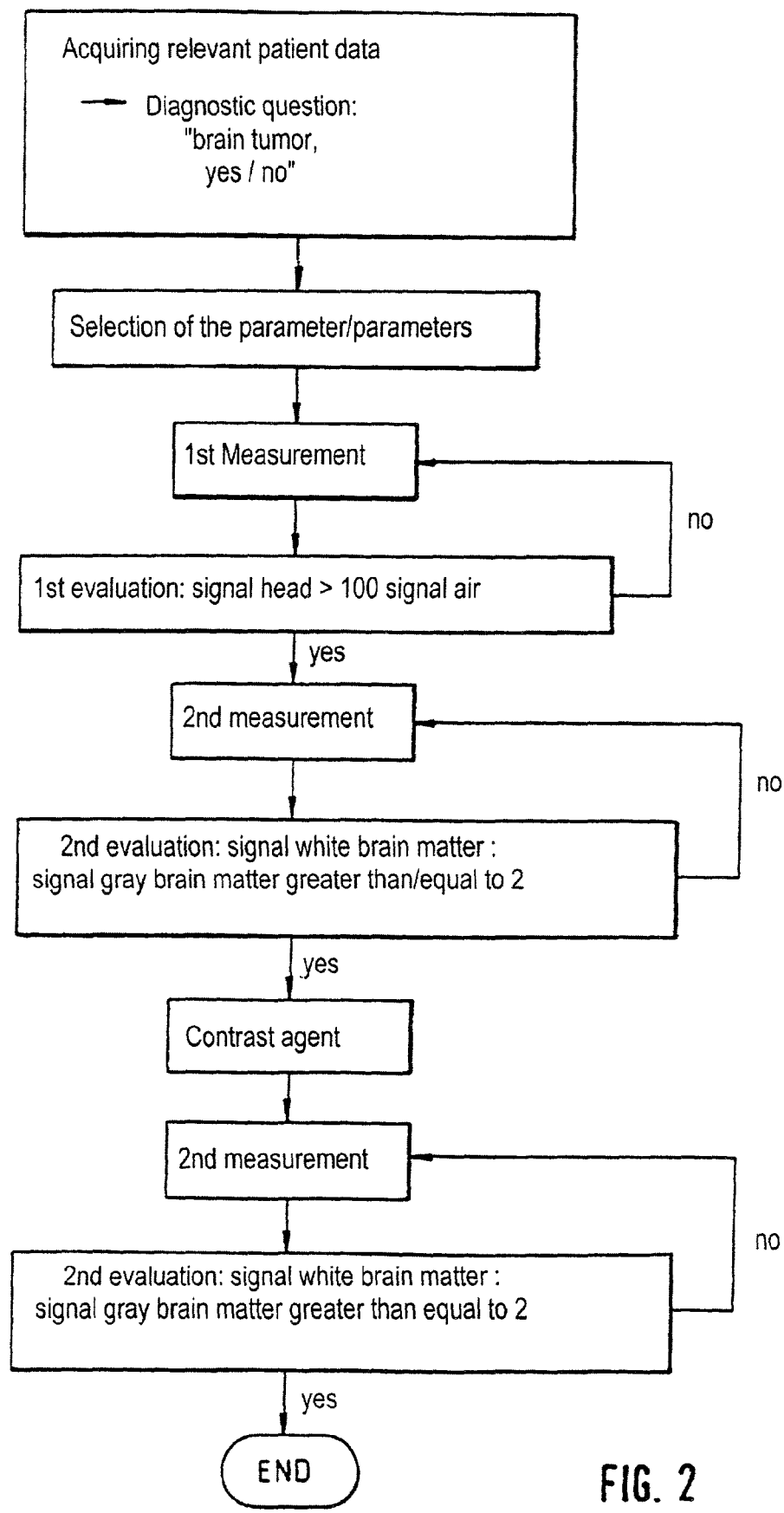
FIG. 2 is a flow chart of a second exemplary examination conducted in accordance with the inventive method using an inventive apparatus.

FIG. 2 shows another inventive exemplary embodiment. Here, as well, the relevant patient data are acquired in the first step. The diagnostic question here is: "brain tumor, yes/no". After the patient data have been acquired, the selection of the parameter or parameters ensues. In the illustrated exemplary embodiment, two different parameters that define the minimum contrast to be achieved are selected.

The first measurement or the first registration of the images or of the image series ensues after the parameter selection. After a specific number x of images have been registered, these are subsequently interpreted in the framework of a first evaluation in view of the first, selected parameter. A check is made to determine whether the image contrast reaches a first minimum value. To this end, a check is made to determine whether the signal amplitudes that represent the image regions that show the head amount to at least one hundred times the signal in air. Since air actually supplies no signal, a de facto check is made to determine whether the head signal corresponds to at least one hundred times the background noise. If the first implementation indicates thereto that this minimum contrast is not yet established, the first measurement is continued. When the minimum contrast is set, the second measurement ensues and can be implemented given different system operating parameters. After implementation of a specific number x of measurements, and thus registration of individual images, the second evaluation ensues with reference to the second, initially selected parameter. A check is thereby made to determine whether the signal or the signal amplitude of the image regions that show the white brain matter is greater than or equal to 2 in relation to the signal of the image regions that show the grey brain mater. If this is not the case, i.e. when a ratio 2:1 in view of the signal amplitudes is not established, even more second measurements are undertaken. The evaluation to determine whether the minimum contrast has now been achieved subsequently ensues anew.

When the second evaluation then shows that the prescribed ratio has been met, then a contrast agent is administered in the illustrated exemplary embodiment, this emphasizing a potential brain tumor even more clearly. After the administration of the contrast agent, the second measurement is implemented anew or further measurements are implemented with the same operating parameters, after which a new evaluation occurs. This is based on the same parameter as in the preceding evaluation. As assumed, the signal ratio of white brain matter to grey brain matter then likewise lies in the required range; however, only the potential tumor region is more clearly visible on the basis of the administration of the contrast agent. Subsequently, the measurement is ended. If the minimum contrast, however, has not yet been reached, then further measurements ensue.

The two exemplary embodiments are only examples and are not limiting. Arbitrary quality parameters of any type whatsoever can be employed with respect to which the registered images are image series can be interpreted in situ during the course of the image registration process, and a further control of the registration operation ensues dependent on the evaluation result. The quality parameters are fundamentally based on individual image-related or image-series related aspects or define these aspects, since the goal of the inventive method is to enable an optimally constant and reproducible image registration with qualitatively comparable image qualities.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for operating a medical imaging examination apparatus comprising the steps of:
   sequentially acquiring measured signals from an examination subject;
   processing said measured signals in an image computer to obtain image data signals from said measured signals, and forming at least one diagnostic image from said image data for review to make a diagnosis relative to said examination subject;
   setting a predetermined parameter that is specific to said diagnosis and that represents a criterion for image quality of said at least one diagnostic image;
   automatically electronically analyzing said at least one diagnostic image to determine whether said at least one diagnostic image has an image quality which satisfies said parameter;
   if said at least one diagnostic image has an image quality which satisfies said parameter, ending acquisition of said measured signals; and
   if said at least one diagnostic image has an image quality which does not satisfy said parameter, acquiring further measured signals until a diagnostic image having an image quality which satisfies said parameter is obtained.

2. A method as claimed in claim 1 comprising setting a continuation limit and aborting said continued acquisition of said measured signals if said continuation limit is exceeded without a diagnostic image being obtained having an image quality which satisfies said parameter.

3. A method as claimed in claim 2 comprising setting a time span as said continuation limit.

4. A method as claimed in claim 2 comprising setting a predetermined number of unsuccessful attempts to obtain a diagnostic image having an image quality which satisfies said parameter, as said continuation limit.

5. A method as claimed in claim 1 comprising employing a parameter representing contrast in said at least one diagnostic image as said parameter representing a criterion for image quality.

6. A method as claimed in claim 5 wherein said at least one diagnostic image has two image regions having respective grey scale values, and comprising employing a parameter defining a relationship of the respective grey scale values of said two image regions as said parameter representing contrast in said at least one diagnostic image.

7. A method as claimed in claim 1 wherein said image computer generates an image data signal containing said image data, and comprising setting a predetermined further parameter related to said image data signal, and automatically electronically analyzing said at least one diagnostic image to determine whether both said parameter representing a criterion for image quality and said further parameter are satisfied, and wherein the step of ending said measured signal acquisition comprises ending said measured signal acquisition only if both of said parameter representing a criterion for image quality and said further parameter are satisfied, and wherein the step of continuing acquisition of said measured signals comprises continuing acquisition of said measured signals until a diagnostic image is obtained having an image quality which satisfies said parameter representing a criterion for image quality and an image data signal which satisfies said further parameter.

8. A method as claimed in claim 7 wherein said image data signal has a waveform having a signal amplitude, signal edges each having a slope, and a waveform width, and comprising selecting said further parameter as a parameter defining at least one of said amplitude, said slope, and a ratio of said amplitude to said waveform width.

9. A method as claimed in claim 1 wherein said image computer generates a plurality of diagnostic images from said measured signals, and comprising the additional steps of:
   checking image stability by automatically electronically analyzing at least two of said plurality of diagnostic images to identify a change of said parameter between said at least two diagnostic images;
   setting a change limit and automatically electronically determining whether said change exceeds said change limit, and wherein the step of ending said measured signal acquisition comprises ending said measured signal acquisition if said parameter is satisfied and said change limit is not exceeded, and wherein the step of continuing to acquire measured signals comprises continuing to acquire said measured signals if said change limit is exceeded until at least two further diagnostic images are obtained wherein said change limit is not exceeded.

10. A method as claimed in claim 1 wherein the step of acquiring measured signals from said examination subject comprises acquiring nuclear magnetic resonance signals from said examination subject as said measured signals.

11. A medical imaging examination apparatus comprising:
   a signal acquisition arrangement for sequentially acquiring measured signals from an examination subject;
   an image computer supplied with said measured signals for processing said measured signals to obtain image data signals from said measured signals, said image computer forming at least one diagnostic image from said image data signals for review to make a diagnosis relative to said examination subject;
   a processor having an input unit for setting a predetermined, diagnosis-specific parameter that is specific to said diagnosis and that represents a criterion for image quality of said at least one diagnostic image;
   said processor automatically analyzing said at least one diagnostic image to determine whether said at least one diagnostic image has an image quality which satisfies said parameter, and, if said at least one diagnostic image has an image quality which satisfies said parameter, said processor generating a signal to said signal acquisition arrangement for ending acquisition of said measured signals and, if said at least one diagnostic image has an image quality which does not satisfy said parameter, said processor causing said signal acquisition arrangement to acquire further measured signals until a diagnostic image having an image quality which satisfies said parameter is obtained.

12. A medical imaging examination apparatus as claimed in claim 11 wherein said input unit allows setting of a continuation limit and wherein said processor aborts said continued acquisition of said measured signals if said continuation limit is exceeded without a diagnostic image being obtained having an image quality which satisfies said parameter.

13. A medical imaging examination apparatus as claimed in claim 12 wherein said input unit allows setting of a time span as said continuation limit.

14. A medical imaging examination apparatus as claimed in claim 12 wherein said input unit allows setting of a predetermined number of unsuccessful attempts to obtain a diagnostic image having an image quality which satisfies said parameter, as said continuation limit.

15. A medical imaging examination apparatus as claimed in claim 11 wherein said processor employs a parameter representing contrast in said at least one diagnostic image as said parameter representing a criterion for image quality.

16. A medical imaging examination apparatus as claimed in claim 11 wherein said at least one diagnostic image has two image regions having respective grey scale values, and wherein said processor employs a parameter defining a relationship of the respective grey scale values of said two image regions as said parameter representing contrast in said at least one diagnostic image.

17. A medical imaging examination apparatus as claimed in claim 11 wherein said input unit allows setting of a predetermined further parameter related to said image data signals, and wherein said processor automatically analyzes said at least one diagnostic image to determine whether both said parameter representing a criterion for image quality and said further parameter are satisfied, and wherein said processor generates said signal ending said measured signal acquisition only if both of said parameter representing a criterion for image quality and said further parameter are satisfied, and wherein said processor causes said signal acquisition arrangement to continue acquisition of said measured signals until a diagnostic image is obtained having an image quality which satisfies said parameter representing a criterion for image quality and an image data signal which satisfies said further parameter.

18. A medical imaging examination apparatus as claimed in claim 17 wherein said image data signal has a waveform having a signal amplitude, signal edges each having a slope, and a waveform width, and wherein said processor employs a parameter as said further parameter that defines at least one of said amplitude, said slope, and a ratio of said amplitude to said waveform width.

19. A medical imaging examination apparatus as claimed in claim 11 wherein said image computer generates a plurality of diagnostic images from said measured signals, and wherein said processor checks image stability by automatically analyzing at least two of said plurality of diagnostic images to identify a change of said parameter between said at least two diagnostic images and wherein said input unit allows setting of a change limit and said processor automatically determines whether said change exceeds said change limit, and wherein said processor generates said signal ending said measured signal acquisition if said parameter is satisfied and said change limit is not exceeded, and wherein said processor causes said signal acquisition arrangement to continue to acquire measured signals if said change limit is exceeded until at least two further diagnostic images are obtained wherein said change limit is not exceeded.

20. A medical imaging examination apparatus as claimed in claim 11 wherein said signal acquisition arrangement acquires nuclear magnetic resonance signals from said examination subject as said measured signals.

* * * * *